(12) United States Patent
Ootake et al.

(10) Patent No.: US 10,556,076 B2
(45) Date of Patent: Feb. 11, 2020

(54) CUFF PRESSURE ADJUSTING DEVICE

(71) Applicant: ICST CORPORATION, Saitama-shi, Saitama (JP)

(72) Inventors: Yusuke Ootake, Saitama (JP); Hiroshi Nakase, Saitama (JP)

(73) Assignee: ICST CORPORATION (JP)

(*) Notice: Subject to any disclaimer, the term of this patent is extended or adjusted under 35 U.S.C. 154(b) by 70 days.

(21) Appl. No.: 15/552,548

(22) PCT Filed: Feb. 22, 2016

(86) PCT No.: PCT/JP2016/055048
§ 371 (c)(1),
(2) Date: Aug. 22, 2017

(87) PCT Pub. No.: WO2016/136665
PCT Pub. Date: Sep. 1, 2016

(65) Prior Publication Data
US 2018/0339121 A1 Nov. 29, 2018

(30) Foreign Application Priority Data
Feb. 25, 2015 (JP) .................. 2015-035333

(51) Int. Cl.
*A61M 16/04* (2006.01)
*A61M 25/10* (2013.01)
*A61M 16/00* (2006.01)

(52) U.S. Cl.
CPC ........ *A61M 16/044* (2013.01); *A61M 16/024* (2017.08); *A61M 25/10181* (2013.11);
(Continued)

(58) Field of Classification Search
CPC ................ A61M 16/04; A61M 16/044; A61M 16/0434; A61M 16/0463;
(Continued)

(56) References Cited

U.S. PATENT DOCUMENTS 3,613,668 A * 10/1971 Beck .................... A61B 5/0235
600/498
3,896,791 A * 7/1975 Ono ........................ A61B 5/022
174/47

(Continued)

FOREIGN PATENT DOCUMENTS

JP  2007-105495 A  4/2007
JP  2010-057817 A  3/2010
(Continued)

OTHER PUBLICATIONS

Covidien Japan Inc., "high low hand cuff pressure gauge II", [online], Pharmaceuticals and Medical Devices Agency, [searched on Feb. 25, 2015], Internet <URL:http://www.info.pmda.go.jp/ygo/pack/610015/13B1X00069VB001A_A_09_01/>.

(Continued)

*Primary Examiner* — Samchuan C Yao
*Assistant Examiner* — Margaret M Luarca
(74) *Attorney, Agent, or Firm* — Harness, Dickey & Pierce, P.L.C.

(57) ABSTRACT

A cuff pressure adjusting device includes: a gas feeding unit which feeds a gas into a cuff by a pressing manipulation performed by a user; a cuff pressure detection unit which detects a pressure in the cuff; and a display unit which displays the pressure detected by the cuff pressure detection unit. The gas feeding unit includes: an elastic hollow body which is deformed so as to reduce an inner volume with reception of a pressing manipulation; and a support member which is disposed adjacently to the elastic hollow body in a direction along which the pressing manipulation is performed.

12 Claims, 7 Drawing Sheets

(52) U.S. Cl.
CPC ............. *A61M 25/10186* (2013.11); *A61M 25/10188* (2013.11); *A61M 2205/18* (2013.01); *A61M 2205/3331* (2013.01); *A61M 2205/583* (2013.01); *A61M 2205/587* (2013.01); *A61M 2205/8212* (2013.01)

(58) Field of Classification Search
CPC ........ A61M 25/10181; A61M 25/1018; A61M 25/10183; A61M 25/10184; A61M 25/01182; A61M 25/10187; A61M 2205/583; A61M 2205/587; A61M 2205/3331; A61M 2016/0027; A61M 5/152; A61B 5/02141; A61B 5/0225; A61B 5/742; F04B 45/02; F04B 45/06; F04B 33/00
USPC ..................................... 604/98.02, 100.01
See application file for complete search history.

(56) References Cited

U.S. PATENT DOCUMENTS

| | | | | |
|---|---|---|---|---|
| 4,598,707 | A * | 7/1986 | Agdanowski | A61M 16/04 128/207.15 |
| 5,487,383 | A * | 1/1996 | Levinson | A61M 16/044 128/204.23 |
| 7,250,039 | B2 * | 7/2007 | Fitzgerald | A61M 5/282 604/192 |
| 7,892,202 | B2 * | 2/2011 | Lampropoulos | A61M 25/10182 604/100.01 |
| 2008/0119745 | A1 * | 5/2008 | Yang | A61B 5/02141 600/493 |
| 2011/0109458 | A1 * | 5/2011 | Shipman | A61M 16/044 340/573.1 |
| 2011/0152700 | A1 * | 6/2011 | Sawanoi | A61B 5/02225 600/493 |
| 2011/0178419 | A1 * | 7/2011 | Wood | A61B 5/08 600/529 |
| 2012/0017897 | A1 | 1/2012 | Ranganathan et al. | |
| 2013/0092166 | A1 | 4/2013 | Pearce | |
| 2014/0261442 | A1 * | 9/2014 | Graboi | A61M 16/044 128/207.15 |
| 2014/0261443 | A1 * | 9/2014 | Lowenstein | A61M 16/044 128/207.15 |
| 2014/0275820 | A1 * | 9/2014 | Varga | A61M 16/0078 600/301 |
| 2015/0320949 | A1 | 11/2015 | Jaffe | |

FOREIGN PATENT DOCUMENTS

| | | |
|---|---|---|
| JP | 2013-536000 A | 9/2013 |
| JP | 2015-503388 A | 2/2015 |
| WO | WO-2014-102874 A1 | 7/2014 |

OTHER PUBLICATIONS

Exception to lack of novelty of invention filed in Japan regarding Japanese Application No. 2015-035333; filed Mar. 27, 2014; 43 pages.

* cited by examiner

CUFF PRESSURE ADJUSTING DEVICE

CROSS REFERENCE TO RELATED APPLICATIONS

This is a U.S. National Stage Application of PCT/JP2016/055048, filed on Feb. 22, 2016, which claims priority to Japanese Patent Application No. 2015-035333, filed on Feb. 25, 2015. The entire disclosures of the above applications are incorporated herein by reference.

TECHNICAL FIELD

The present invention relates to a cuff pressure adjusting device which adjusts a pressure in a cuff mounted on an endotracheal tube (tracheostomy tube) or the like to be inserted into a trachea in performing intubation or a tracheostomy.

BACKGROUND ART

Conventionally, in performing artificial respiration with respect to a patient who is having difficulty in breathing spontaneously, intubation or a tracheostomy is performed such that an endotracheal tube (tracheostomy tube) is inserted into the trachea of the patient so as to secure an airway, and an artificial respirator or the like is connected to the endotracheal tube. FIG. 7 is a view showing one example of a conventionally used general endotracheal tube 100.

As shown in the drawing, the endotracheal tube 100 includes: a tube 101; a connector 102 for connecting an artificial respirator or the like, which is mounted on one end (proximal end) of the tube 101; a cuff 103 mounted on the other end (distal end) of the tube 101; an inflation tube 104 through which air is introduced into the cuff 103 so as to inflate the cuff 103 (inflation); a pilot balloon 105 mounted on the inflation tube 104 on a side opposite to the cuff 103; and a luer valve 106.

Among these elements, the cuff 103 is inflated after the tube 101 is inserted into the trachea so as to block an upper airway and a lower airway from each other so that the cuff 103 allows efficient feeding of air or the like into the lungs and, at the same time, prevents secretions such as saliva from entering the lower airway. In inflating the cuff 103, a method is generally adopted where the cuff 103 is inflated by a syringe which is connected to the luer valve 106 and, at the same time, whether or not the cuff 103 is inflated at a proper internal pressure (cuff pressure) is confirmed by touch obtained by pressing the pilot balloon 105 with a finger.

When a cuff pressure is excessively low, there arises a problem that not only air or the like which is to be fed into the lungs leaks into the upper airway, but also secretions or the like enter the lower airway thus causing an infectious disease or the like. On the other hand, when a cuff pressure is excessively high, there arises a problem that the tracheal mucosa is pressed thus being damaged. Accordingly, it is generally recommended that a cuff pressure is controlled within a range of from 22 to 32 cmH$_2$O.

In view of the above, in recent years, to control a cuff pressure more accurately, the number of medical institutions has increased that use a dedicated cuff pressure gauge (endotracheal tube cuff inflator) provided with a squeeze bulb for introducing air into the cuff 103 and a pressure gauge in place of a syringe (see non patent literature Covidien Japan Inc., "high low hand cuff pressure gauge II", [online], Pharmaceuticals and Medical Devices Agency, [searched on Feb. 25, 2015], Internet <URL:http://www.info.pmda.go.jp/ygo/pack/610015/13B1X00069VB001A_A_09_01/>, for example).

However, in conventional cuff pressure gauges such as a cuff pressure gauge described in the above-mentioned non patent literature, in many cases, convenience of use is not taken into account in detail and hence, there exists a problem that it may be difficult to rapidly and accurately perform fine adjustment of a cuff pressure. Particularly, the cuff pressure gauge includes a squeeze bulb having an excessively larger volume than a volume of the cuff 103 so that a cuff pressure is liable to be excessively increased even with a single pressing manipulation of the squeeze bulb. Accordingly, it is necessary to slowly and carefully perform the pressing manipulation.

Further, the conventional cuff pressure gauges are not significantly designed to take into account fail-safe and fool-proof measures. Accordingly, when a health care provider having little experience uses the cuff pressure gauge or when a general person uses the cuff pressure gauge for in-home care or the like, there exists a problem that the manipulation is required to be performed more carefully and, at the same time, it takes time to acquire a feeling for proper manipulation.

The present invention has been made in view of such circumstances, and it is an object of the present invention to provide a cuff pressure adjusting device where convenience of use and safety are enhanced.

SUMMARY

The present invention is directed to a cuff pressure adjusting device characterized by including: a gas feeding unit configured to feed a gas into a cuff by a pressing manipulation performed by a user; a cuff pressure detection unit configured to detect a pressure in the cuff; and a display unit configured to display the pressure detected by the cuff pressure detection unit, wherein the gas feeding unit includes: an elastic hollow body configured to be deformed so as to reduce an inner volume of the elastic hollow body with reception of the pressing manipulation; and a support member disposed adjacently to the elastic hollow body in a direction along which the pressing manipulation is performed.

The present invention is also characterized in that, in the cuff pressure adjusting device according to the present solution, the elastic hollow body is formed into a flat shape which substantially conforms to at least a portion of an outer surface of the support member.

The present invention is also characterized by, in the cuff pressure adjusting device according to the present solution, further including a power supply unit disposed in the support member, and configured to supply an electric power to the cuff pressure detection unit and the display unit.

The present invention is also characterized in that, in the cuff pressure adjusting device according to the present solution, the support member includes a bulging portion configured to bulge toward the elastic hollow body, and the elastic hollow body includes a recessed portion configured to store at least a portion of the bulging portion.

The present invention is also characterized by, in the cuff pressure adjusting device according to the present solution, further including: a forced release opening through which the gas in the cuff is made to flow out to an outside of the cuff pressure adjusting device; and a switching unit configured to switch a connection of the cuff between a connection with the elastic hollow body and a connection with the forced release opening.

The present invention is also characterized in that, in the cuff pressure adjusting device according to the present solution, the switching unit is formed of a solenoid valve configured to connect the cuff and the elastic hollow body with each other in a non-excited state, and configured to connect the cuff and the forced release opening with each other in an excited state.

The present invention is also characterized by, in the cuff pressure adjusting device according to the present solution, further including a gas release valve configured to allow the gas in the cuff to flow out to the outside of the cuff pressure adjusting device by a manipulation performed by a user, wherein the gas release valve is disposed on a side close to the cuff with respect to the switching unit.

The present invention is also characterized by, in the cuff pressure adjusting device according to the present solution, further including a control unit configured to control the cuff pressure detection unit, the display unit and the switching unit, wherein the control unit includes pressurization stop means configured to control the switching unit such that the cuff and the forced release opening are connected with each other when a pressure detected by the cuff pressure detection unit is larger than a predetermined upper limit pressure.

The present invention is also characterized in that, in the cuff pressure adjusting device according to the present solution, the control unit includes: sleep means configured to bring the cuff pressure adjusting device into a sleep state where at least display on the display unit is stopped when the cuff pressure detection unit does not detect a pressure of equal to or more than a predetermined first threshold value within a predetermined determination period in a normal operation state; and return means configured to make the cuff pressure adjusting device return to the normal operation state when the cuff pressure detection unit detects a pressure of equal to or more than a predetermined second threshold value in the sleep state.

The present invention is also characterized by, in the cuff pressure adjusting device according to the present solution, further including a pressing manipulation detection unit configured to detect the pressing manipulation, wherein the return means is configured to make the cuff pressure adjusting device return to the normal operation state with a detection of the pressing manipulation by the pressing manipulation detection unit in the sleep state.

The present invention is also characterized by, in the cuff pressure adjusting device according to the present solution, further including a pressing manipulation detection unit configured to detect the pressing manipulation, wherein the cuff pressure adjusting device is configured to be activated with the detection of the pressing manipulation by the pressing manipulation detection unit.

The present invention is also characterized in that, in the cuff pressure adjusting device according to the present solution, the cuff pressure detection unit includes two pressure detectors, and the control unit includes abnormality determination means configured to determine that an abnormality is generated when a difference between outputs from two pressure detectors exceeds a predetermined range.

The present invention is also characterized by, in the cuff pressure adjusting device according to the present solution, further including a light emitting section configured to emit light under control of the control unit, wherein the control unit includes notification means configured to control the light emitting section so as to change a light emitting mode corresponding to the pressure detected by the cuff pressure detection unit.

The present invention is also characterized in that, in the cuff pressure adjusting device according to the present solution, the light emitting section is used also as a backlight illumination configured to illuminate the display unit from a back side of the display unit.

Advantageous Effect of Invention

According to the cuff pressure adjusting device of the present invention, it is possible to acquire an excellent advantageous effect that convenience of use and safety can be enhanced.

DETAILED DESCRIPTION

Hereinafter, an embodiment of the present invention is described with reference to attached drawings.

Figure 1A:
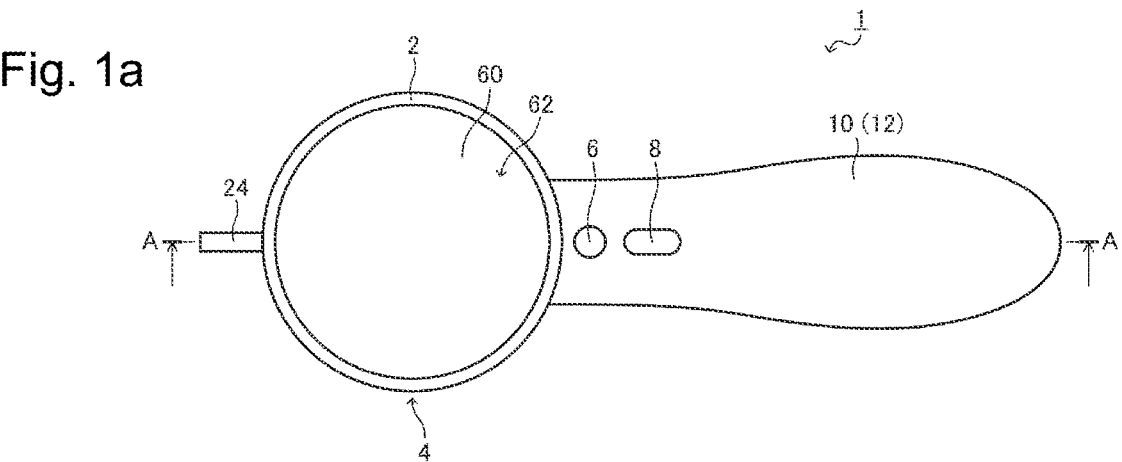
FIG. 1(a) is a schematic plan view of a cuff pressure adjusting device according to an embodiment of the present invention.
Figure 1B:
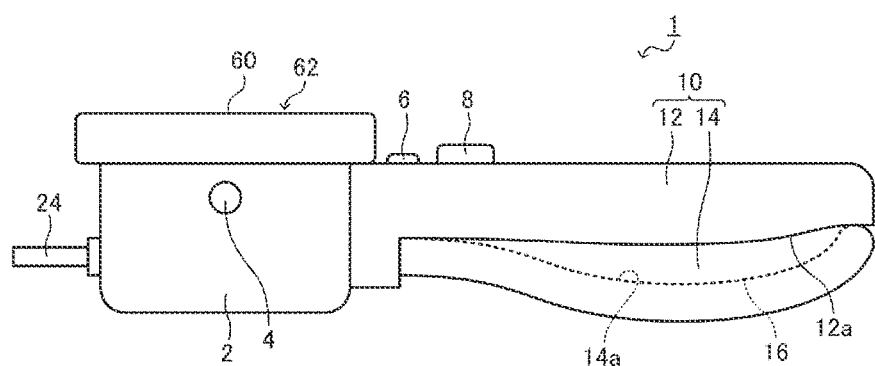
FIG. 1(b) is a schematic front view of the cuff pressure adjusting device.
Figure 1C:
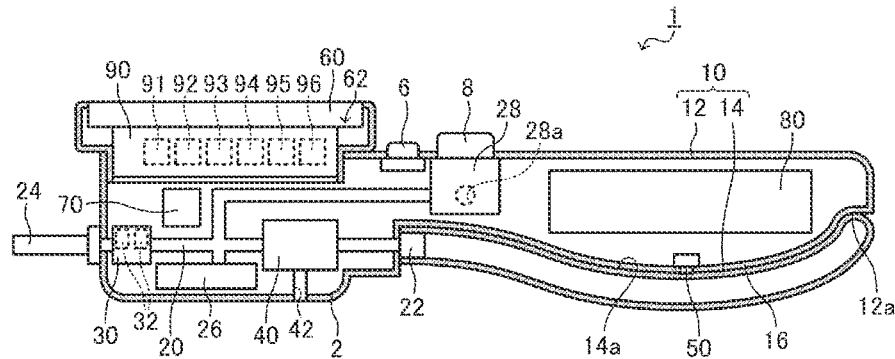
FIG. 1(c) is a cross-sectional view of the cuff pressure adjusting device taken along a line A-A in FIG. 1(a).

FIG. 1(a) is a schematic plan view of a cuff pressure adjusting device 1 according to this embodiment. FIG. 1(b) is a schematic front view of the cuff pressure adjusting device 1. FIG. 1(c) is a cross-sectional view of the cuff pressure adjusting device 1 taken along a line A-A in FIG. 1(a). As shown in these drawings, the cuff pressure adjusting device 1 includes: a gas feeding unit 10; a flow passage 20; a cuff pressure detection unit 30; a switching unit 40; a pressing manipulation detection unit 50; a display unit 60; a sound output unit 70; a power supply unit 80; and a control unit 90.

The gas feeding unit 10 introduces a gas (air) into a cuff 103 by a pressing manipulation performed by a user. In this embodiment, the gas feeding unit 10 is configured such that a user holds the cuff pressure adjusting device 1 by gripping the gas feeding unit 10 with one hand, and the user tightens his grip without changing hand position so that air can be introduced into the cuff 103. To describe in more detail, the gas feeding unit 10 includes a support member 12 formed into a substantially rod shape and an elastic hollow body 14 disposed below the support member 12 in an adjacent manner.

The support member 12 forms a part of a casing 2 which stores the flow passage 20, the cuff pressure detection unit 30 and other parts, and is made of a material having suitable rigidity such as a resin. The support member 12 is a portion which is held by a user so that the support member 12 is formed into a substantially rod shape having a substantially spindle shape as viewed in a plan view so as to allow the user to easily grip the support member 12. Further, a bulging portion 16 which bulges toward the elastic hollow body 14 is formed on a lower surface 12a of the support member 12.

The elastic hollow body 14 is a squeeze bulb formed of a suitable elastic body made of rubber, a resin or the like. That is, the elastic hollow body 14 is a kind of pump which is configured such that when the elastic hollow body 14 is pressed from the outside, the elastic hollow body 14 is deformed so as to reduce an inner volume of the elastic hollow body 14 thus discharging air toward the flow passage 20. The elastic hollow body 14 is connected to the flow passage 20 disposed in the casing 2 by way of an inner connection portion 22. The elastic hollow body 14 has a check valve not shown in the drawing. Accordingly, the elastic hollow body is configured such that when the elastic hollow body 14 restores after being deformed once, the elastic hollow body 14 takes in air from an outside space, and does not take in air from the flow passage 20.

The elastic hollow body 14 is formed into a flat shape having a recessed portion 14a which stores the bulging portion 16, and the elastic hollow body 14 is disposed substantially along the lower surface 12a forming a part of an outer surface of the support member 12. In this embodiment, the elastic hollow body 14 is formed as described above and hence, without impairing the ease of gripping the gas feeding unit 10, an amount of air discharged by a single pressing manipulation (that is, a single gripping manipulation) is reduced. With such a configuration, a possibility of a cuff pressure being excessively increased can be reduced and hence, convenience of use and safety of the cuff pressure adjusting device 1 can be enhanced.

The casing 2 is provided with a power supply button 4, a mode switching button 6 and a release button 8. The power supply button 4 is provided for performing a switching manipulation for turning on and turning off a power supply. The mode switching button 6 is provided for performing a switching manipulation for switching an operation mode of the cuff pressure adjusting device 1. The release button 8 is provided for performing a releasing manipulation for releasing a pressure in the cuff 103. In this embodiment, the support member 12 of the gas feeding unit 10 is provided with the mode switching button 6 and the release button 8 so that these buttons are disposed at positions which allow a user to manipulate these buttons with his thumb in a state where the user grips the gas feeding unit 10. Further, the power supply button 4 is disposed at a position away from the mode switching button 6 and the release button 8 so that it is possible to prevent the power supply being carelessly turned off by an erroneous manipulation during use of the cuff pressure adjusting device 1.

The flow passage 20 is a passage through which air discharged from the elastic hollow body 14 flows, and the flow passage 20 is disposed in the casing 2. The inner connection portion 22 connected to the elastic hollow body 14 is formed on one end of the flow passage 20, and an outer connection portion 24 connected to a luer valve 106 is formed on the other end of the flow passage 20. Of these connection portions 22, 24, the inner connection portion 22 is provided with a check valve which prevents air from flowing into the elastic hollow body 14 from the flow passage 20. A buffer tank 26 and a gas release valve 28 are provided at a middle portion of the flow passage 20, and the cuff pressure detection unit 30 and the switching unit 40 are connected to the middle portion of the flow passage 20.

The buffer tank 26 is a tank formed with a predetermined volume and disposed in the casing 2, and the buffer tank 26 absorbs a rapid pressure change and a rapid flow rate change which occur when the pressing manipulation of the elastic hollow body 14 is performed. The gas release valve 28 is a valve which releases the flow passage 20 to the atmosphere through a release opening 28a thus releasing a pressure in the cuff 103 to the outside. The gas release valve 28 is configured to be opened and closed by a manipulation of the above-mentioned release button 8. The gas release valve 28 may be formed of a valve which is mechanically opened and closed by a manipulation of the release button 8, or may be a solenoid valve or the like which is electrically opened and closed by a manipulation of the release button 8.

The cuff pressure detection unit 30 detects a cuff pressure, that is, a pressure in the cuff 103. The cuff pressure detection unit 30 includes two pressure detectors 32 electrically connected to the control unit 90, and each of these two pressure detectors 32 transmits a signal output corresponding to a detected pressure to the control unit 90. The control unit 90 compares two signal outputs with each other and, when a difference between two signal outputs falls within a predetermined range, the control unit 90 derives a cuff pressure from either one of two signal outputs or an average between two signal outputs. When a difference between two signal outputs exceeds the predetermined range, the control unit 90 determines that an abnormality is generated in the detection of a cuff pressure, and issues an alarm.

In this embodiment, the cuff pressure detection unit 30 includes two pressure detectors 32 and compares two signal outputs with each other as described above. Accordingly, even when an abnormality is generated in the pressure detector 32, such an abnormality can be immediately obtained so that safety can be increased. A structure of the pressure detector 32 is not particularly limited, and any of various known pressure sensors may be adopted as the pressure detector 32. It may be also possible to adopt the configuration where the flow passage 20 is branched, and the pressure detector 32 is connected to the branched flow passage 20.

The switching unit 40 switches a connection of the outer connection portion 24 (that is, cuff 103) between a connection with the elastic hollow body 14 and a connection with a forced release opening 42. That is, the switching unit 40 switches a state of the cuff pressure adjusting device 1 between a state where a pressure in the cuff 103 can be maintained or increased due to a connection of the outer connection portion 24 with the elastic hollow body 14 and a state where a pressure in the cuff 103 is released to the outside thus being lowered due to a connection of the outer connection portion 24 with the forced release opening 42 which is open to the outside of the casing 2.

In this embodiment, with the provision of the switching unit 40 as described above, a pressure in the cuff 103 can be forcibly lowered and, at the same time, it is possible to set a state where air is not introduced into the cuff 103 even with a pressing manipulation of the elastic hollow body 14. With such a configuration, convenience of use and safety of the cuff pressure adjusting device 1 are enhanced. In this embodiment, the switching unit 40 is formed of a 3-port solenoid valve. However, a structure of the switching unit 40 is not particularly limited, and it may be possible to adopt another known structure such as a structure where a plurality of solenoid valves are combined with each other.

The switching unit 40 is connected to the flow passage 20 at a position more on the elastic hollow body 14 side than the cuff pressure detection unit 30 and the gas release valve 28 are connected. Accordingly, even when the outer connection portion 24 is connected with the forced release opening 42 by means of the switching unit 40, the cuff pressure detection unit 30 can detect a cuff pressure. When the gas release valve 28 is also opened in a state where the outer connection portion 24 is connected with the forced release opening 42, a cuff pressure can be lowered more rapidly.

The pressing manipulation detection unit 50 detects a pressing manipulation of the elastic hollow body 14. In this embodiment, the pressing manipulation detection unit 50 is formed of a suitable detection switch, and is disposed on the elastic hollow body 14 side of the support member 12. That is, the pressing manipulation detection unit 50 is configured such that a switch is turned on by being pressed along with the pressing manipulation of the elastic hollow body 14 thus detecting that the pressing manipulation of the elastic hollow body 14 is performed.

In this embodiment, with the provision of the pressing manipulation detection unit 50 as described above, the cuff pressure adjusting device 1 can be activated from a power-supply-off state or can be returned from a sleep state in response to a pressing manipulation of the elastic hollow body 14. With such a configuration, convenience of use and safety of the cuff pressure adjusting device 1 are enhanced. A structure of the pressing manipulation detection unit 50 is not particularly limited, and any of various known switches or the like may be adopted as the pressing manipulation detection unit 50. The pressing manipulation detection unit 50 may detect that a pressing manipulation of the elastic hollow body 14 is performed by detecting an increase in pressure in the elastic hollow body 14 or an air flow which flows out from the elastic hollow body 14.

The display unit 60 displays a cuff pressure detected by the cuff pressure detection unit 30 and, at the same time, displays various other information. In this embodiment, the display unit 60 is formed of a liquid crystal display device, and the display unit 60 includes a backlight 62 which can emit light of three colors consisting of red, blue and green. The backlight 62 is made to emit light of a different color corresponding to the pressure detected by the cuff pressure detection unit 30. Accordingly, even when a user does not read display on the display unit 60, the user can quickly recognize the current level of cuff pressure. With such a configuration, convenience of use and safety of the cuff pressure adjusting device 1 are enhanced.

The display unit 60 may display the cuff pressure detected by the cuff pressure detection unit 30 as a numerical value, or may display the cuff pressure in an analog manner by displaying a needle, a bar or the like. In place of the liquid crystal display device, another display device such as an electronic paper may be adopted as the display unit 60, for example.

The sound output unit 70 outputs various sounds, and includes a suitable speaker. In this embodiment, both emission of light from the backlight 62 and an output mode of a notification sound from the sound output unit 70 vary corresponding to the pressure detected by the cuff pressure detection unit 30. That is, in this embodiment, even when a user does not visually recognize the display unit 60, the user can quickly recognize the current level of cuff pressure. With such a configuration, convenience of use and safety of the cuff pressure adjusting device 1 are enhanced.

The power supply unit 80 supplies an electric power for operating the cuff pressure detection unit 30, the switching unit 40, the pressing manipulation detection unit 50, the display unit 60, the sound output unit 70, the control unit 90 and the like. To be more specific, the power supply unit 80 is formed of two AA batteries and a battery holder which holds these batteries. However, any of various other primary batteries or any of various other secondary batteries may be adopted. Further, a configuration may be adopted where the casing 2 is provided with a terminal for charging secondary batteries thus allowing the secondary batteries to be charged while being stored in the casing 2.

The power supply unit 80 is disposed in the support member 12 of the gas feeding unit 10. In this embodiment, the power supply unit 80, which is relatively heavy, is disposed in the support member 12. Accordingly, a space in the casing 2 is effectively used so that the cuff pressure adjusting device 1 is formed in a compact manner and, at the same time, the weight balance of the cuff pressure adjusting device 1 is optimized. That is, the cuff pressure adjusting device 1 is formed in a compact manner and, further, the position of the center of gravity is set close to the gas feeding unit 10 which is gripped by the user. With such a configuration, a moment generated when a user holds the cuff pressure adjusting device 1 with his hand can be reduced and hence, a massive feeling can be reduced and, at the same time, manipulation feeling of lightness can be realized.

The control unit 90 includes a CPU, a ROM, a RAM and the like, and controls the whole cuff pressure adjusting device 1. As functional configurations realized with the execution of a program stored in the ROM or the like by the CPU, the control unit 90 includes, in addition to basic control means 91 which performs a basic control of respective parts of the cuff pressure adjusting device 1, pressurization stop means 92, sleep means 93, return means 94, abnormality determination means 95, and notification means 96.

The pressurization stop means 92 controls the switching unit 40 such that, when the pressure detected by the cuff pressure detection unit 30 is larger than a predetermined first pressure (upper limit pressure), the outer connection portion 24 (that is, cuff 103) and the forced release opening 42 are connected with each other. With such a control, the pressurization stop means 92 forcibly lowers a pressure in the cuff 103 and, at the same time, prevents an increase in cuff pressure even with a pressing manipulation of the gas feeding unit 10. The sleep means 93 stops display on the display unit 60, emission of light from the backlight 62 and an output from the sound output unit 70 when a pressure of equal to or more than a predetermined first threshold value (5 cmH$_2$O in this embodiment) is not detected within a predetermined determination period (one minute in this embodiment) with the cuff pressure adjusting device 1 in a normal operation state. With such an operation, the sleep means 93 brings the cuff pressure adjusting device 1 into a sleep state (electric power saving state).

The return means 94 makes the cuff pressure adjusting device 1 return to the normal operation state from the sleep state when the cuff pressure detection unit 30 detects a pressure of equal to or more than a predetermined second threshold value (5 cmH$_2$O in this embodiment), when the pressing manipulation detection unit 50 detects a pressing manipulation of the elastic hollow body 14, or when the power supply button 4 is operated with the cuff pressure adjusting device 1 in the sleep state. The abnormality determination means 95 determines that an abnormality is generated when a state where a difference between outputs from two pressure detectors 32 falls outside a predetermined range (±4 cmH$_2$O in this embodiment) continues for a predetermined period (2 seconds in this embodiment). With such determination, the abnormality determination means 95 makes the backlight 62 emit light in a predetermined mode (blinking red in this embodiment) and, at the same time, outputs a predetermined alarm sound from the sound output unit 70 thus notifying the generation of an abnormality.

The notification means 96 controls the backlight 62 so as to change a light emitting mode corresponding to the pressure detected by the cuff pressure detection unit 30 and, at the same time, controls the sound output unit 70 so as to change an output mode of a notification sound corresponding to the pressure detected by the cuff pressure detection unit 30. With such controls, the notification means 96 notifies the current level of cuff pressure separately from display of the cuff pressure on the display unit 60.

In this embodiment, as operation modes of the control unit 90, three modes consisting of a T mode, an L mode and an F mode are set. With respect to these operation modes, the T (Tracheal) mode is an operation mode where a pressure adjustment of the cuff 103 mounted on an endotracheal tube 100 is assumed, and the L (Laryngeal) mode is an operation mode where the cuff pressure adjusting device 1 is optimized for performing a pressure adjustment of a cuff mounted on a laryngeal mask. That is, the cuff pressure adjusting device 1 of this embodiment can be also used for a cuff pressure adjustment of a laryngeal mask where a larynx is closed by a cuff so that a tube is not inserted into a trachea.

In the T mode and the L mode, the notification means 96 makes the backlight 62 emit light in green when the cuff pressure is less than a predetermined second pressure (lower limit pressure), makes the backlight 62 emit light in red when the cuff pressure is larger than the above-mentioned first pressure (upper limit pressure), and makes the backlight 62 emit light in blue when the cuff pressure is equal to or more than the second pressure and equal to or less than the first pressure. Further, the notification means 96 makes the sound output unit 70 output a notification sound of one second duration once every two seconds when the cuff pressure is less than the second pressure, makes the sound output unit 70 continuously output the notification sound when the cuff pressure is larger than the first pressure, and makes the sound output unit 70 output no notification sound when the cuff pressure is equal to or more than the second pressure and equal to or less than the first pressure.

In the T mode, the first pressure is set to 32 cmH$_2$O which is an upper limit value of a recommended pressure of the cuff 103 of the endotracheal tube 100, and the second pressure is set to 22 cmH$_2$O which is a lower limit value of the recommended pressure. In the L mode, the first pressure is set to 60 cmH$_2$O which is an upper limit value of a recommended pressure of the cuff of the laryngeal mask, and the second pressure is set to 50 cmH$_2$O which is a lower limit value of the recommended pressure. That is, in the T mode and the L mode, the notification means 96 performs a notification by the backlight 62 and the sound output unit 70 in a different notification mode corresponding to a case where the cuff pressure is lower than the recommended pressure range, a case where the cuff pressure falls within the recommended pressure range, and a case where the cuff pressure is higher than the recommended pressure range.

Accordingly, in the T mode and the L mode, a user can rapidly recognize, without reading display on the display unit 60, whether or not the cuff pressure falls within the recommended pressure range and whether the cuff pressure is lower or higher than the recommended pressure range when the cuff pressure falls outside the recommended pressure range. Further, in the T mode and the L mode, when the cuff pressure exceeds the recommended pressure range, as described above, the pressurization stop means 92 controls the switching unit 40 so as to connect the forced release opening 42 with the outer connection portion 24 and hence, the cuff pressure is automatically lowered.

The F (Free) mode is an operation mode for allowing a user to use the cuff pressure adjusting device 1 in the same manner as a conventional cuff pressure gauge. In the F mode, only the first pressure is set to 122 cmH$_2$O which is an upper limit value in measuring a pressure by the cuff pressure adjusting device 1. In the F mode, when the cuff pressure is equal to or less than the first pressure, the notification means 96 makes the backlight 62 emit light in green and, at the same time, makes the sound output unit 70 output no notification sound. Further, in the F mode, when the cuff pressure is larger than the first pressure, the notification means 96 makes the backlight 62 emit light in red and, at the same time, makes the sound output unit 70 continuously output the notification sound. Accordingly, the user can rapidly recognize that the cuff pressure is beyond a measurement upper limit value without reading display on the display unit 60. Further, in the F mode, when the cuff pressure exceeds the measurement upper limit value, as described above, the pressurization stop means 92 controls the switching unit 40 so as to connect the forced release opening 42 and the outer connection portion 24 with each other thus lowering a pressure in the cuff 103.

In this embodiment, the T mode is set as a default operation mode so that, immediately after the power supply is turned on, the control unit 90 is operated in the T mode. After the power supply is turned on, each time the mode switching button 6 is manipulated, the operation mode is switched by rotating through the order of T mode, L mode, F mode and T mode.

Figure 2A:
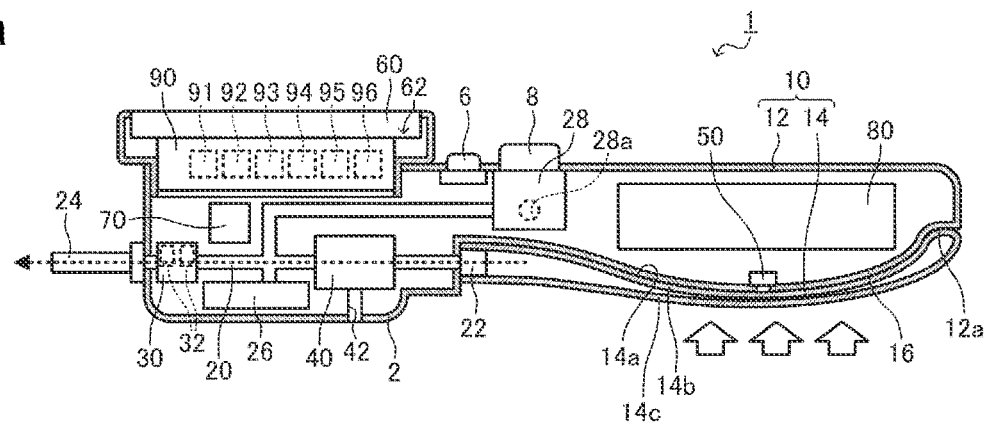
FIGS. 2(a) to 2(c) are schematic cross-sectional views showing the manner of operation of the cuff pressure adjusting device.
Figure 2B:
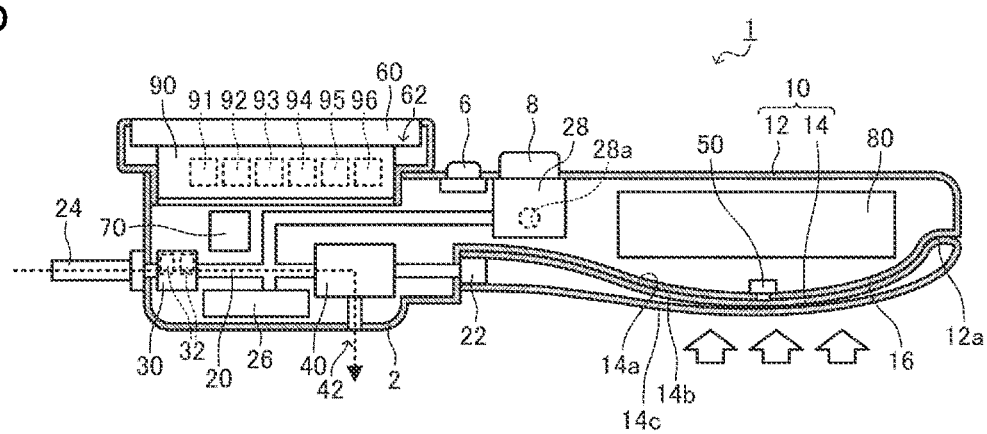
Figure 2C:
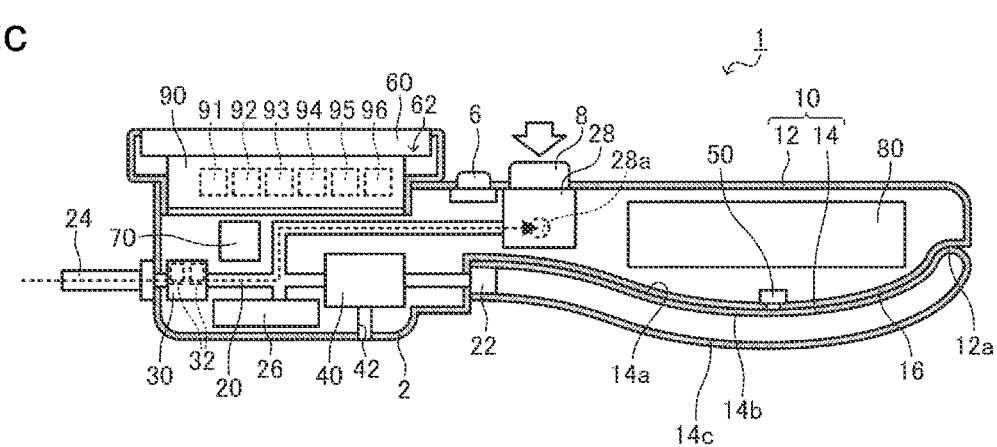

FIGS. 2(a) to 2(c) are schematic cross-sectional views showing the manner of operation of the cuff pressure adjusting device 1, and are cross-sectional views of the cuff pressure adjusting device 1 taken along a line A-A in FIG. 1(a). FIG. 2(a) shows a state where the switching unit 40 connects the elastic hollow body 14 with the outer connection portion 24. In inflating the cuff 103, the elastic hollow body 14 is pressed toward the support member with a hand gripping the gas feeding unit 10 in such a state, and the elastic hollow body 14 is deformed so as to reduce an inner volume of the elastic hollow body 14. With such deformation, air in the elastic hollow body 14 is pushed out toward the flow passage 20 so that the air is fed into the cuff 103.

Next, when a pressing force with respect to the elastic hollow body 14 is released, the elastic hollow body 14 is returned to the original shape due to a restoring force of the elastic deformation and, due to a negative pressure generated at that time, air outside the cuff pressure adjusting device 1 is introduced into the elastic hollow body 14 through a check valve not shown in the drawing. In this manner, the elastic hollow body 14 is filled with air to be discharged by a next pressing manipulation.

In this embodiment, the elastic hollow body 14 is formed into a flat shape and hence, even when the elastic hollow body 14 is deformed until a support-member-side outer wall 14b and a support-member-opposing-side outer wall 14c which opposedly face each other are brought into contact with each other, only a small amount of air is fed to the cuff 103. To be more specific, the elastic hollow body 14 is set such that, when a pressing manipulation where the support-member-side outer wall 14b and the support-member-opposing-side outer wall 14c are brought into contact with each other is performed three to six or more times, a pressure in the cuff 103 (cuff pressure) mounted on the general endotracheal tube 100 exceeds an upper limit (first pressure)

of the recommended pressure. With such a configuration, a possibility of a cuff pressure being excessively increased is lowered.

Further, in this embodiment, the elastic hollow body 14 is formed into a flat shape so as to shorten a stroke (distance) of a single pressing manipulation and hence, the pressing manipulation and the subsequent refilling of the elastic hollow body 14 with air due to the restoration of the elastic hollow body 14 can be performed rapidly. The support member 12 is disposed adjacently to the elastic hollow body 14 in the pressing direction (the vertical direction in this embodiment) so that the support member 12 is made to function as a stopper of the pressing manipulation and hence, a user can clearly recognize an end of a single pressing manipulation. That is, a user can not only rapidly perform a pressing manipulation a plurality of times, but also surely feed a predetermined amount of air into the cuff 103 with each single pressing manipulation. Further, the elastic hollow body 14 is formed into a flat shape and, at the same time, the support member 12 is made to function as the stopper and hence, a pressing manipulation can be simply and accurately detected by the pressing manipulation detection unit 50 formed of any of various known switches or the like.

FIG. 2(*b*) shows a state where the switching unit 40 connects the forced release opening 42 with the outer connection portion 24. In such a state, air in the cuff 103 flows out to the outside through the forced release opening 42 so that a cuff pressure is lowered. Further, in such a state, the elastic hollow body 14 and the outer connection portion 24 are blocked from each other by the switching unit 40 and hence, even when the elastic hollow body 14 is deformed, air discharged from the elastic hollow body 14 is not fed into the cuff 103. That is, in this embodiment, by switching a connection of the outer connection portion 24 by the switching unit 40, not only a cuff pressure is forcibly lowered, but also an increase in cuff pressure is prevented even when the elastic hollow body 14 is deformed by an erroneous manipulation or the like. When the pressing manipulation of the elastic hollow body 14 is performed in a state where the switching unit 40 connects the forced release opening 42 with the outer connection portion 24, a pressure in the elastic hollow body 14 is increased and hence, a user can recognize a connection state of the switching unit 40 also by a different response in performing the pressing manipulation.

It is needless to say that a port communicating with the forced release opening 42 is closed in the state where the switching unit 40 connects the elastic hollow body 14 with the outer connection portion 24, and a port communicating with the flow passage 20 on the elastic hollow body 14 side is closed in a state where the switching unit 40 connects the forced release opening 42 with the outer connection portion 24.

FIG. 2(*c*) shows a state where the gas release valve 28 is opened by manipulating the release button 8. In this manner, by opening the gas release valve 28, air in the cuff 103 flows out to the outside through the release opening 28*a* so that a cuff pressure is lowered. That is, in this embodiment, fine adjustment of a cuff pressure can be performed by the manipulation of the release button 8.

Figure 3A:
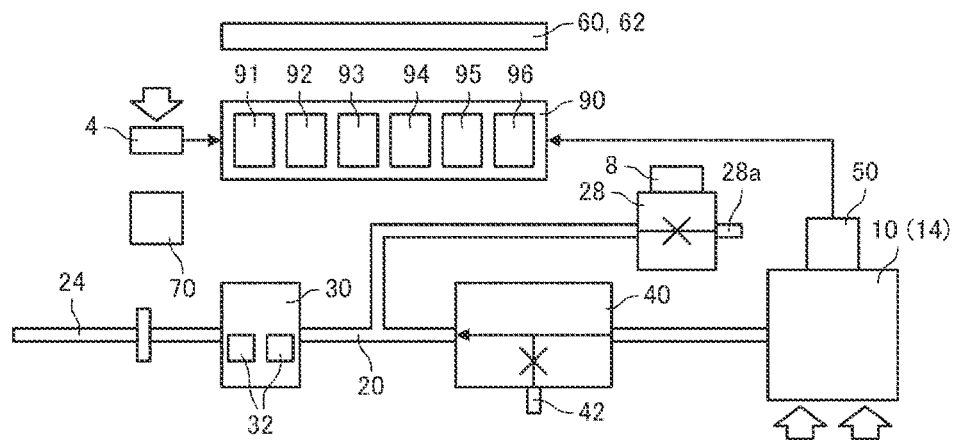
FIGS. 3(a) to 3(c) are block diagrams showing a state under control of a control unit.
Figure 3B:
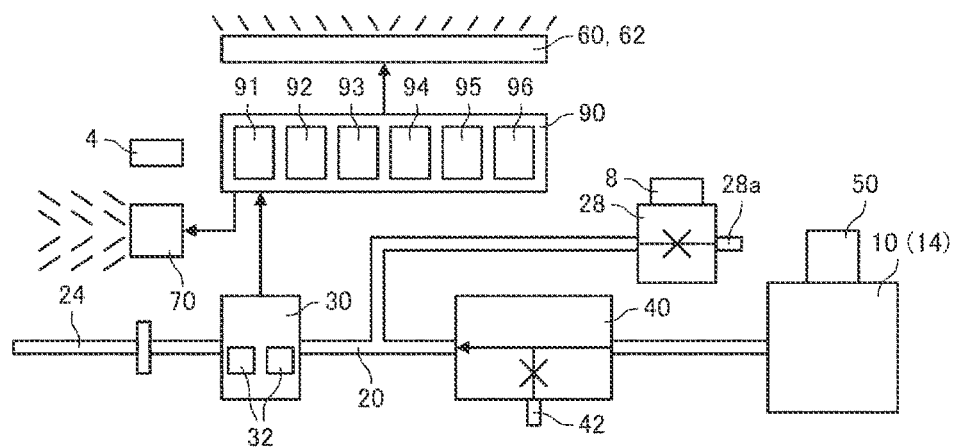
Figure 3C:
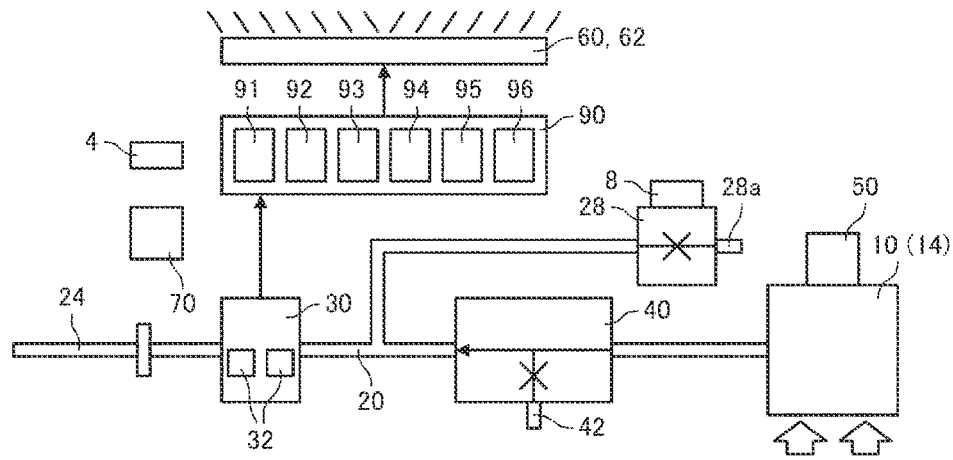

Next, a control performed by the control unit 90 is described in detail following the use procedure of the cuff pressure adjusting device 1. FIGS. 3(*a*) to 3(*c*), FIGS. 4(*a*) to 4(*c*) and FIGS. 5(*a*) and 5(*b*) are block diagrams showing a state under control of the control unit 90. In a power-supply-off state, the cuff pressure adjusting device 1 is in a state where the switching unit 40 connects the outer connection portion 24 and the elastic hollow body 14 with each other. That is, in this embodiment, a solenoid valve forming the switching unit 40 connects the outer connection portion 24 and the elastic hollow body 14 with each other in a non-excited state, and connects the outer connection portion 24 and the forced release opening 42 with each other in an excited state.

The outer connection portion 24 is connected to the luer valve 106 of the endotracheal tube 100 and, thereafter, in the power-supply-off state as shown in FIG. 3(*a*), when the power supply is turned on by the manipulation of the power supply button 4 or the pressing manipulation of the gas feeding unit 10 by a user, an electric power in the power supply unit 80 is supplied to respective parts of the cuff pressure adjusting device 1, and the control unit 90 sets an operation mode to a T mode and starts a control of the respective parts. That is, the cuff pressure adjusting device 1 is activated.

To be more specific, as shown in FIG. 3(*b*), the basic control means 91 of the control unit 90 controls the cuff pressure detection unit 30 so as to receive signal outputs from the cuff pressure detection unit 30. Then, the basic control means 91 derives a cuff pressure based on the signal outputs received from the cuff pressure detection unit 30. The basic control means 91 also controls the display unit 60 so as to make the display unit 60 display the current cuff pressure detected by the cuff pressure detection unit 30 and, at the same time, to make the display unit 60 display various other information such as a remaining amount of a battery, for example.

The abnormality determination means 95 of the control unit 90 compares the signal outputs from two pressure detectors 32 of the cuff pressure detection unit 30. When a difference between these signal outputs falls outside a predetermined range, the abnormality determination means 95 controls the backlight 62 and the sound output unit 70 so as to issue an alarm. The notification means 96 of the control unit 90 controls the backlight 62 and the sound output unit 70 based on the cuff pressure detected by the cuff pressure detection unit 30 so as to notify the current level of cuff pressure. Usually, a cuff pressure immediately after the power supply is turned on is less than the second pressure. Accordingly, the notification means 96 makes the backlight 62 emit light in green and, at the same time, makes the sound output unit 70 output a notification sound of one second duration once every two seconds.

After the power supply is turned on, as shown in FIG. 3(*c*), a cuff pressure is increased by the pressing manipulation of the gas feeding unit 10 performed by a user. In this embodiment, the cuff pressure adjusting device 1 can be activated from the power-supply-off state also by the pressing manipulation of the gas feeding unit 10. Accordingly, after the cuff pressure adjusting device 1 is activated, the pressing manipulation of the gas feeding unit 10 for adjusting a cuff pressure can be rapidly performed as a series of operations from the activation of the cuff pressure adjusting device 1.

As a result of the pressing manipulation performed by a user, when the cuff pressure detected by the cuff pressure detection unit 30 becomes equal to or more than the second pressure and equal to or less than the first pressure, the notification means 96 changes the light emission of the backlight 62 from green to blue and, at the same time, stops the output of a notification sound from the sound output unit 70. With such operations, the user can easily recognize that the cuff pressure is beyond the second pressure which is a lower limit of the recommended pressure, and substantially falls within a range of the recommended pressure.

Figure 4A:
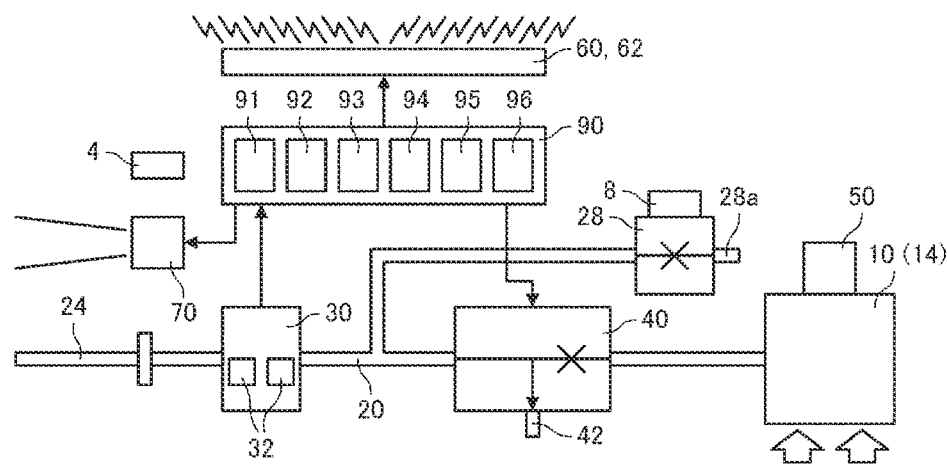
FIGS. 4(a) to 4(c) are block diagrams showing a state under control of the control unit.
Figure 4B:
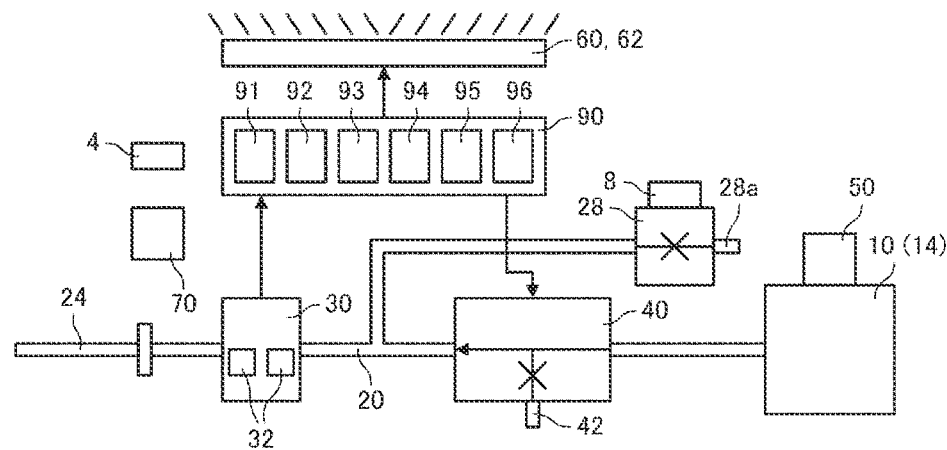
Figure 4C:
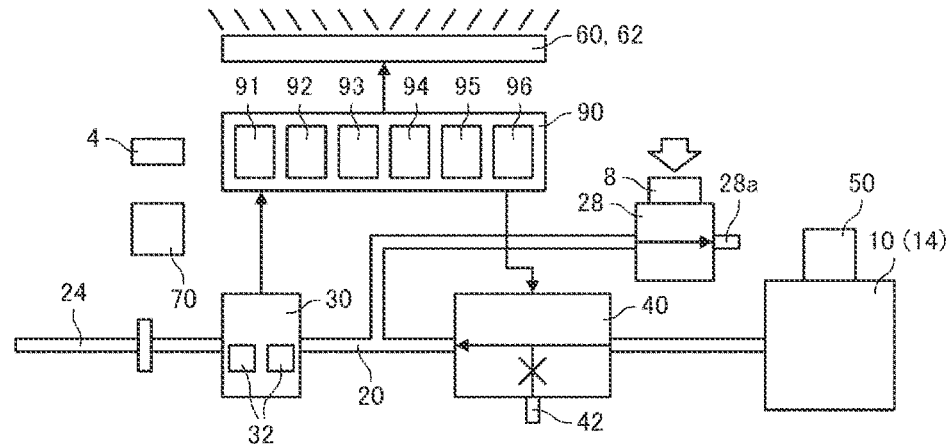

As a result of the continuous pressing manipulations of the gas feeding unit 10 by a user, when a detected cuff pressure becomes larger than the first pressure, as shown in FIG. 4(*a*), the pressurization stop means 92 of the control unit 90 brings the switching unit 40 into the excited state so as to connect the forced release opening 42 with the outer connection portion 24. With such operations, a cuff pressure is lowered to a pressure of equal to or less than the first pressure and, at the same time, a cuff pressure cannot be increased even with a pressing manipulation of the gas feeding unit 10. Accordingly, it is possible to surely prevent excessive increase in cuff pressure exceeding the first pressure which is an upper limit of the recommended pressure.

When the detected cuff pressure becomes larger than the first pressure, the notification means 96 of the control unit 90 changes the light emission of the backlight 62 from blue to red and, at the same time, makes the sound output unit 70 continuously output a notification sound. With such operations, a user can easily recognize that a cuff pressure is beyond the first pressure which is the upper limit of the recommended pressure.

Thereafter, when the detected cuff pressure becomes equal to or more than the second pressure and equal to or less than the first pressure due to the flowing out of air through the forced release opening 42, as shown in FIG. 4(*b*), the pressurization stop means 92 of the control unit 90 brings the switching unit 40 into the non-excited state so as to connect the elastic hollow body 14 with the outer connection portion 24. With such operations, the flowing out of air through the forced release opening 42 is stopped, and a cuff pressure is maintained. Further, the notification means 96 changes the light emission of the backlight 62 from red to blue and, at the same time, stops the output of a notification sound from the sound output unit 70.

Thereafter, as shown in FIG. 4(*c*), by manipulating the release button 8, the user can perform fine adjustment of the cuff pressure within a range of equal to or more than the second pressure and equal to or less than the first pressure. When the cuff pressure is lowered to a pressure less than the second pressure by the manipulation of the release button 8, the notification means 96 of the control unit 90 changes the light emission of the backlight 62 from blue to green and, at the same time, makes the sound output unit 70 output a notification sound of one second duration once every two seconds. Accordingly, the user can easily recognize excessive lowering of the cuff pressure and, in such a case, the user can increase the cuff pressure again by performing the pressing manipulation of the gas feeding unit 10.

When adjustment of the cuff pressure is completed, the user removes the outer connection portion 24 from the luer valve 106, and turns off the power supply by manipulating the power supply button 4. With such operations, the operation of the control unit 90 is ended. On the other hand, after the outer connection portion 24 is removed from the luer valve 106, when the power supply button 4 is not manipulated for a predetermined determination period, the sleep means 93 of the control unit 90 brings the cuff pressure adjusting device 1 into a sleep state (electric power saving state).

Figure 5A:
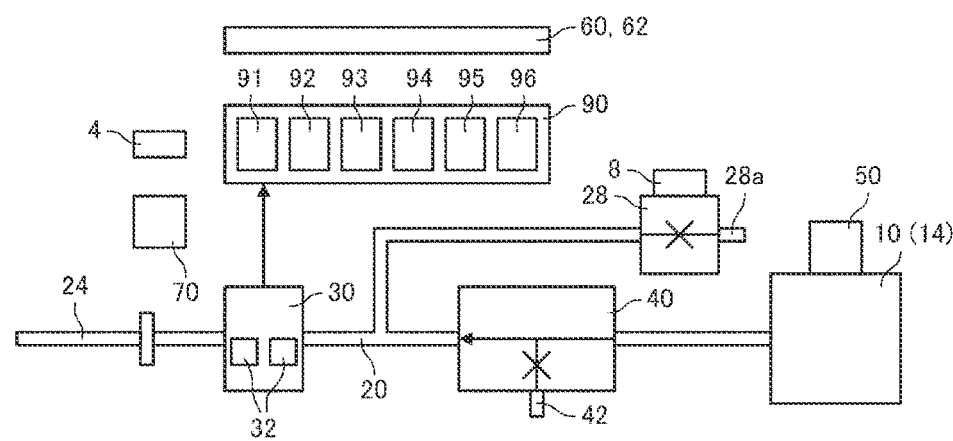
FIGS. 5(a) and 5(b) are block diagrams showing a state under control of the control unit.
Figure 5B:
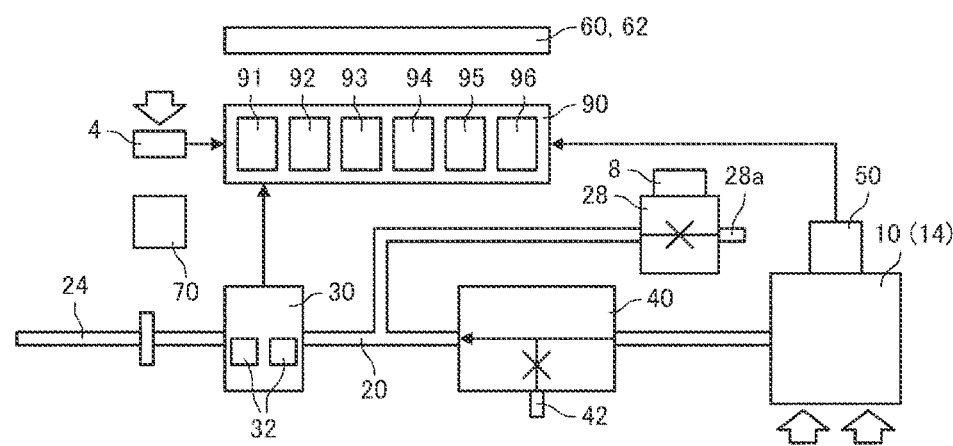

To be more specific, when a power-supply-on state continues even after the outer connection portion 24 is removed from the luer valve 106, the pressure detected by the cuff pressure detection unit 30 becomes a substantially atmospheric pressure (0 cmH$_2$O). Accordingly, when a state where the pressure detected by the cuff pressure detection unit 30 is equal to or less than the first threshold value continues for the predetermined determination period, as shown in FIG. 5(*a*), the sleep means 93 of the control unit 90 stops display on the display unit 60, the light emission of the backlight 62 and the output from the sound output unit 70, and makes the cuff pressure adjusting device 1 shift to the sleep state where the switching unit 40 is in the non-excited state. Also in the sleep state, the basic control means 91 causes the cuff pressure detection unit 30 to continuously detect a cuff pressure.

As shown in FIG. 5(*b*), returning of the cuff pressure adjusting device 1 from the sleep state is performed by the connection of the outer connection portion 24 to the pressurized cuff 103, the manipulation of the power supply button 4, or the pressing manipulation of the gas feeding unit 10. As a result of the connection of the outer connection portion 24 to the luer valve 106, when the cuff pressure detection unit 30 detects a cuff pressure of equal to or more than the second threshold value, the return means 94 of the control unit 90 makes the cuff pressure detection device 1 shift to a normal operation state where display on the display unit 60, the light emission of the backlight 62, the output from the sound output unit 70 and the like are performed. The return means 94 makes the cuff pressure detection device 1 shift to the normal operation state from the sleep state also when the power supply button 4 is manipulated and when the pressing manipulation detection unit 50 detects the pressing manipulation of the gas feeding unit 10.

As described above, the cuff pressure adjusting device 1 is returned to the normal operation state from the sleep state in response to the connection to the pressurized cuff or the pressing manipulation of the gas feeding unit 10 in addition to the manipulation of the power supply button 4 and hence, the cuff pressure adjusting device 1 can be returned from the sleep state more rapidly. Particularly, the cuff pressure adjusting device 1 is returned from the sleep state in response to a pressing manipulation of the gas feeding unit 10 and hence, after the cuff pressure adjusting device 1 is returned, the pressing manipulation of the gas feeding unit 10 for adjusting a cuff pressure can be rapidly performed as a series of operations from the returning of the cuff pressure adjusting device 1.

The control performed by the control unit 90 in the L mode differs from the above-mentioned control only with respect to the setting of the first pressure and the second pressure, and is substantially equal to the above-mentioned control. The control performed by the control unit 90 in the F mode is also substantially equal to the above-mentioned control except for a point that the second pressure is not set and a point that when the cuff pressure detected by the cuff pressure detection unit 30 is equal to or less than the first pressure, the notification means 96 makes the backlight 62 emit light in green and, at the same time, makes the sound output unit 70 output no notification sound.

Figure 6A:
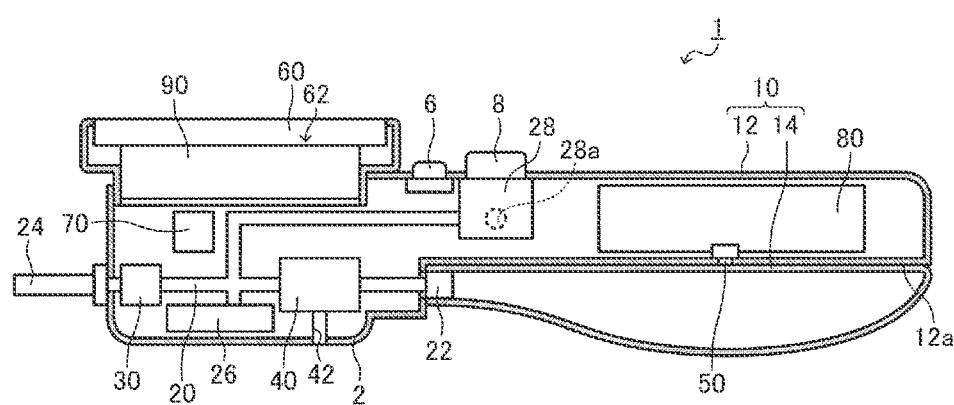
FIGS. 6(a) and 6(b) are schematic cross-sectional views showing an example of another embodiment of the cuff pressure adjusting device.

Next, another embodiment of the cuff pressure adjusting device 1 is described. FIGS. 6(*a*) and 6(*b*) are schematic cross-sectional views showing an example of another embodiment of the cuff pressure adjusting device 1. FIG. 6(*a*) shows one example where the bulging portion 16 is omitted from the support member 12. As described above, the bulging portion 16 is not necessarily provided to the support member 12, and may be omitted corresponding to a shape, size or the like of the support member 12 and the elastic hollow body 14. With the adjustment of a size and a shape of the bulging portion 16 together with the adjustment of a size and a shape of the recessed portion 14*a* of the elastic hollow body 14, an amount of air discharged by a single pressing manipulation of the gas feeding unit 10 and a stroke of the pressing manipulation may be adjusted. In some cases, a surface (lower surface 12a) of the support member 12 on the elastic hollow body 14 side may be recessed.

Figure 6B:
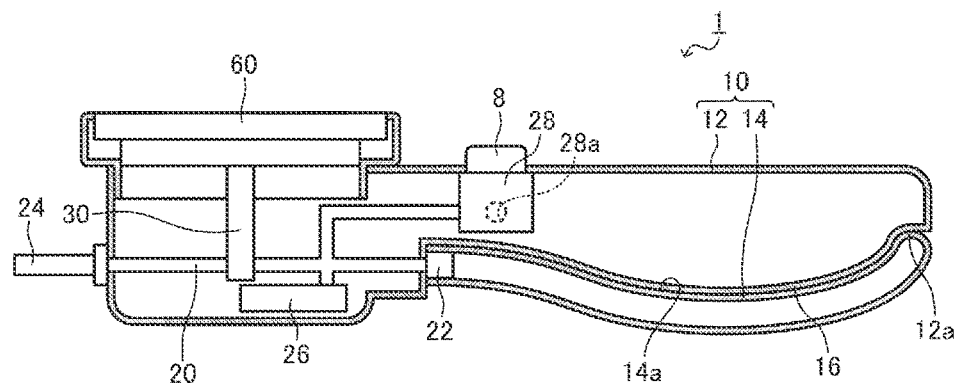
Figure 7:
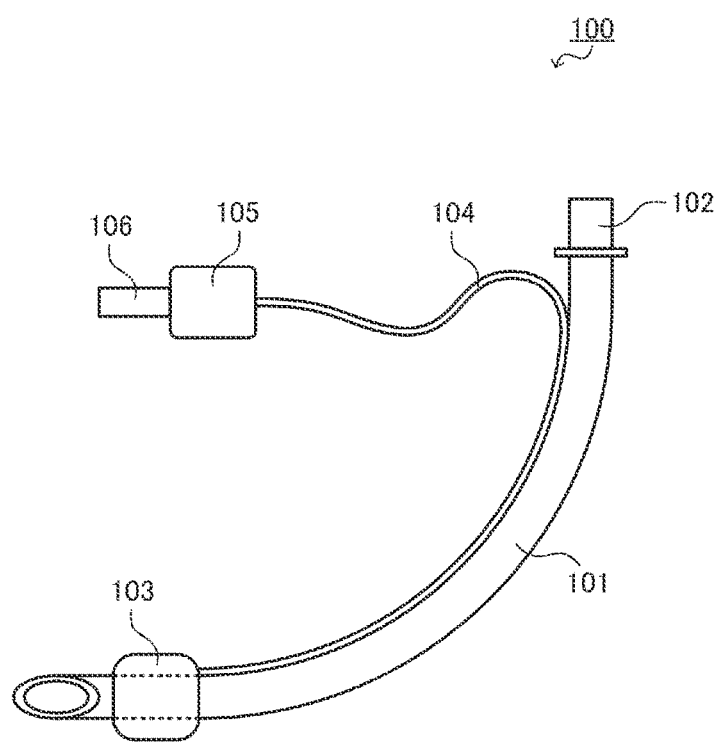
FIG. 7 is a view showing one example of a conventionally used general endotracheal tube.

FIG. 6(b) shows one example where the cuff pressure adjusting device 1 is configured to be mechanically operated. In this example, a mechanical pressure gauge is adopted as the cuff pressure detection unit 30 and the display unit 60 and, at the same time, the switching unit 40, the pressing manipulation detection unit 50, the sound output unit 70, the power supply unit 80 and the control unit 90 are omitted. With the omission of the electric configurations as described above, the cuff pressure adjusting device 1 can be formed in a simple manner with a light weight and, at the same time, a cost can be reduced.

Also in the example shown in FIG. 6(b), the gas feeding unit 10 is formed of the support member 12 and the elastic hollow body 14 disposed adjacently to the support member 12 in the pressing direction. With such a configuration, without impairing the ease of gripping the gas feeding unit 10, an amount of air discharged by a single pressing manipulation and a stroke of the pressing manipulation can be properly adjusted and, at the same time, it is possible to make the support member 12 function as a stopper of the pressing manipulation. Accordingly, compared to a conventional cuff pressure gauge, convenience of use and safety can be enhanced. It is needless to say that the bulging portion 16 may be omitted also in the example shown in FIG. 6(b).

As has been described heretofore, the cuff pressure adjusting device 1 according to this embodiment includes: the gas feeding unit 10 which feeds a gas into the cuff 103 by a pressing manipulation performed by a user; the cuff pressure detection unit 30 which detects a pressure in the cuff 103; and the display unit 60 which displays the pressure detected by the cuff pressure detection unit 30. The gas feeding unit 10 includes: the elastic hollow body 14 which is deformed so as to reduce an inner volume of the elastic hollow body 14 with reception of the pressing manipulation; and the support member 12 which is disposed adjacently to the elastic hollow body 14 in the direction along which the pressing manipulation is performed (vertical direction).

With such a configuration, without impairing the ease of gripping the gas feeding unit 10, an amount of air discharged by a single pressing manipulation and a stroke of the pressing manipulation can be properly adjusted and, at the same time, it is possible to make the support member 12 function as a stopper of the pressing manipulation. Accordingly, a possibility of a cuff pressure being excessively increased can be reduced and, at the same time, it is possible to make the pressing manipulation be easily performed and hence, convenience of use and safety can be enhanced compared with the conventional cuff pressure gauge.

The elastic hollow body 14 is formed into a flat shape which substantially conforms to at least a portion (lower surface 12a) of the outer surface of the support member 12. With such a configuration, without impairing the ease of gripping the gas feeding unit 10, an amount of air discharged by a single pressing manipulation can be suitably reduced and, at the same time, a stroke of the pressing manipulation can be suitably shortened. Accordingly, convenience of use and safety can be enhanced.

The cuff pressure adjusting device 1 also includes the power supply unit 80 which is disposed in the support member 12, and supplies an electric power to the cuff pressure detection unit 30 and the display unit 60. With such a configuration, while detection and display of a cuff pressure are electrically performed, the whole cuff pressure adjusting device 1 can be formed in a compact manner and, at the same time, the weight balance of the cuff pressure adjusting device 1 can be optimized. Accordingly, convenience of use and safety can be enhanced.

The support member 12 includes the bulging portion 16 which bulges toward the elastic hollow body 14, and the elastic hollow body 14 includes the recessed portion 14a which stores at least a portion of the bulging portion 16. With such a configuration, by adjusting a size and a shape of the bulging portion 16 and the recessed portion 14a, an amount of air discharged by a single pressing manipulation and a stroke of the pressing manipulation can be adjusted. Accordingly, both the ease of gripping the gas feeding unit 10 and the ease of performing the pressing manipulation can be highly accomplished.

The cuff pressure adjusting device 1 further includes: the forced release opening 42 through which the gas in the cuff 103 is made to flow out to an outside of the cuff pressure adjusting device 1; and the switching unit 40 which switches a connection of the cuff 103 between a connection with the elastic hollow body 14 and a connection with the forced release opening 42. With such a configuration, a cuff pressure can be forcibly lowered and, at the same time, it is possible to set a state where a cuff pressure is not increased even when the elastic hollow body 14 is deformed. Accordingly, convenience of use and safety can be enhanced.

The switching unit 40 is formed of a solenoid valve which connects the cuff 103 and the elastic hollow body 14 with each other in a non-excited state, and connects the cuff 103 and the forced release opening 42 with each other in an excited state. With such a configuration, it is possible to limit a state where a cuff pressure is forcibly lowered. Accordingly, convenience of use and safety can be enhanced.

The cuff pressure adjusting device 1 further includes the gas release valve 28 which makes the gas in the cuff 103 flow out to the outside of the cuff pressure adjusting device 1 by a manipulation performed by a user, and the gas release valve 28 is disposed on the side close to the cuff 103 with respect to the switching unit 40. With such a configuration, a cuff pressure can be lowered regardless of a state of the switching unit 40. Accordingly, convenience of use and safety can be enhanced.

The cuff pressure adjusting device 1 further includes the control unit 90 which controls the cuff pressure detection unit 30, the display unit 60 and the switching unit 40. The control unit 90 includes the pressurization stop means 92 which controls the switching unit 40 such that the cuff 103 and the forced release opening 42 are connected with each other when the pressure detected by the cuff pressure detection unit 30 is larger than the predetermined upper limit pressure (first pressure). With such a configuration, it is possible to surely prevent an excessive increase in cuff pressure exceeding the upper limit of the recommended pressure. Accordingly, convenience of use and safety can be enhanced.

The control unit 90 includes: the sleep means 93 which brings the cuff pressure adjusting device 1 into a sleep state where at least display of the display unit 60 is stopped when the cuff pressure detection unit 30 do not detect a pressure of equal to or more than the predetermined first threshold value within the predetermined determination period in a normal operation state; and the return means 94 which makes the cuff pressure adjusting device 1 return to the normal operation state when the cuff pressure detection unit 30 detects a pressure of equal to or more than the predetermined second threshold value in the sleep state. With such a configuration, the cuff pressure adjusting device 1 can be rapidly returned from the sleep state. Accordingly, while power consumption is reduced in the sleep state, convenience of use and safety can be enhanced.

The cuff pressure adjusting device 1 further includes the pressing manipulation detection unit 50 which detects a pressing manipulation. The return means 94 makes the cuff pressure adjusting device 1 return to the normal operation state with a detection of the pressing manipulation by the pressing manipulation detection unit 50 in the sleep state. With such a configuration, the cuff pressure adjusting device 1 can be rapidly returned from the sleep state and, at the same time, the pressing manipulation for adjusting a cuff pressure can be rapidly performed as a series of operations from the returning of the cuff pressure adjusting device 1. Accordingly, convenience of use and safety can be enhanced.

The cuff pressure adjusting device 1 also includes the pressing manipulation detection unit 50 which detects a pressing manipulation. The cuff pressure adjusting device 1 is activated with the detection of the pressing manipulation by the pressing manipulation detection unit 50. With such a configuration, the cuff pressure adjusting device 1 can be easily activated from a power-supply-off state and, at the same time, the pressing manipulation for adjusting a cuff pressure can be rapidly performed as a series of operations from the activation of the cuff pressure adjusting device 1. Accordingly, convenience of use and safety can be enhanced.

The cuff pressure detection unit 30 includes two pressure detectors 32. The control unit 90 includes the abnormality determination means 95 which determines that an abnormality is generated when a difference between outputs from two pressure detectors 32 exceeds a predetermined range. With such a configuration, an abnormality relating to the detection of a cuff pressure can be immediately obtained. Accordingly, convenience of use and safety can be enhanced.

The cuff pressure adjusting device 1 further includes the light emitting section (backlight 62) which emits light under control of the control unit 90. The control unit 90 includes the notification means 96 which controls the light emitting section so as to change a light emitting mode corresponding to the pressure detected by the cuff pressure detection unit 30. With such a configuration, a user can easily recognize the current level of cuff pressure without reading display of a cuff pressure on the display unit 60. Accordingly, convenience of use and safety can be enhanced.

The light emitting section is used also as a backlight illumination which illuminates the display unit 60 from a back side of the display unit 60. With such a configuration, notification by the light emitting section can be performed in a mode which allows a user to easily recognize the notification with a configuration that is simple and compact.

Although the embodiment of the present invention has been described heretofore, the cuff pressure adjusting device of the present invention is not limited to the above-mentioned embodiment. It is needless to say that various modifications are conceivable without departing from the gist of the present invention. For example, a shape and an arrangement configuration of respective parts which form the cuff pressure adjusting device 1 are not limited to those described in the above-mentioned embodiment, and other shapes and other arrangement configurations may be adopted.

A shape of the elastic hollow body 14 is not limited to a shape which substantially conforms to the lower surface 12a of the support member 12, and may be a shape which substantially conforms to the outer surface of the support member 12 other than the lower surface 12a. The direction along which the pressing manipulation is performed may be a direction other than the vertical direction. The display unit 60 is not limited to be disposed such that the display unit 60 is directed upward, and may be disposed such that the display unit 60 is directed in another direction.

A light emitting section dedicated to notification may be provided in addition to the backlight 62. For example, a ring-shaped light emitting section may be provided to a periphery of the display unit 60. Further, when the pressure detector 32 has high reliability, the abnormality determination means 95 may be omitted, and the cuff pressure detection unit 30 may include one pressure detector 32.

The manner of operation and advantageous effects described in the above-mentioned embodiment are the enumeration of the most preferable manner of operation and advantageous effects acquired by the present invention, and the manner of operation and advantageous effects of the present invention are not limited to the manner of operation and advantageous effects described in the above-mentioned embodiment.

INDUSTRIAL APPLICABILITY

The cuff pressure adjusting device according to the present invention can be utilized in a medical field for humans or animals.

The invention claimed is:

1. A cuff pressure adjusting device comprising:
a gas feeding member configured to feed a gas into a cuff for respiratory assistance via a tube by a pressing manipulation that is performed by a user, the cuff being disposed in a trachea or a larynx, the gas feeding member being configured with:
an elastic hollow body configured to be deformed so as to reduce an inner volume of the elastic hollow body with reception of the pressing manipulation so that the gas is fed to the cuff via the tube; and
a support member disposed adjacently to the elastic hollow body in a pressing direction along which the pressing manipulation is performed so as to reduce the inner volume of the elastic hollow body by the pressing manipulation, the support member including a bulging outer periphery that outwardly projects toward the elastic hollow body in the pressing direction;
a cuff pressure detection sensor configured to detect a pressure in the cuff;
a pressing manipulation detection switch configured to detect the pressing manipulation; and
an electronic display configured to display the pressure in the cuff detected by the cuff pressure detection sensor,
wherein a gas feeding amount from the gas feeding member to the cuff via the tube by a single stroke of the pressing manipulation causes a pressure increase of the pressure in the cuff, and the pressure increase is equal to or less than 10.67 $cmH_2O$ by the single stroke, and
wherein the pressing manipulation detection switch is provided in the bulging outer periphery of the support member.

2. The cuff pressure adjusting device according to claim 1, further comprising a power supply source disposed in the support member,
wherein the power supply source supplies an electric power to the cuff pressure detection sensor and the electronic display.

3. A cuff pressure adjusting device comprising:
a gas feeding member configured to feed a gas into a cuff for respiratory assistance via a tube by a pressing manipulation performed by a user, the cuff being disposed in a trachea or a larynx, the gas feeding member being configured with:
  an elastic hollow body configured to be deformed so as to reduce an inner volume of the elastic hollow body with reception of the pressing manipulation so that the gas is fed to the cuff via the tube; and
  a support member disposed adjacently to the elastic hollow body in a pressing direction along which the pressing manipulation is performed so as to reduce the inner volume of the elastic hollow body by the pressing manipulation, the support member including a bulging outer periphery that outwardly projects toward the elastic hollow body in the pressing direction;
a cuff pressure detection sensor configured to detect a pressure in the cuff;
a pressing manipulation detection switch configured to detect the pressing manipulation; and
an electronic display configured to display the pressure in the cuff detected by the cuff pressure detection sensor,
wherein the bulging outer periphery is a part of the outer periphery of the support member,
the elastic hollow body has upper and lower outer peripheries, and the upper and lower outer peripheries extend along the bulging outer periphery in a cross-sectional view, and
wherein the pressing manipulation detection switch is provided in the bulging outer periphery of the support member.

4. A cuff pressure adjusting device comprising:
a gas feeding member configured to feed a gas into a cuff for respiratory assistance via a tube by a pressing manipulation performed by a user, the cuff being disposed in a trachea or a larynx, the gas feeding member being configured with:
  an elastic hollow body configured to be deformed so as to reduce an inner volume of the elastic hollow body with reception of the pressing manipulation so that the gas is fed to the cuff via the tube; and
  a support member disposed adjacently to the elastic hollow body in a pressing direction along which the pressing manipulation is performed so as to reduce the inner volume of the elastic hollow body by the pressing manipulation, the support member including a bulging outer periphery that outwardly projects toward the elastic hollow body in the pressing direction;
a cuff pressure detection sensor configured to detect a pressure in the cuff;
a pressing manipulation detection switch configured to detect the pressing manipulation;
an electronic display configured to display the pressure in the cuff detected by the cuff pressure detection sensor;
a forced release opening fluidly communicating with the elastic hollow body and the cuff via the tube, the gas in the cuff being configured to flow out to an outside from the cuff pressure adjusting device through the forced release opening;
a gas flow switch configured to switch a gas flow path between a first path and a second path, the first path allowing fluid communication only between the elastic hollow body and the cuff, the second path allowing the fluid communication only between the cuff and the outside via the forced release opening;
a manual gas release valve that is different from the forced release opening and the gas flow switch, the manual gas release valve being configured to discharge the gas from the cuff to the outside by a manipulation performed by the user; and
a controller configured to:
  receive the detected pressure in the cuff from the cuff pressure detection sensor;
  determine whether the detected pressure is more than a predetermined value; and
  switch the gas flow path from the first path to the second path when the controller determines that the detected pressure is more than the predetermined value,
wherein the pressing manipulation detection switch is provided in the bulging outer periphery of the support member.

5. The cuff pressure adjusting device according to claim 4,
wherein the gas flow switch is a solenoid valve, and
the solenoid valve is configured to fluidly connect the cuff and the elastic hollow body with each other in a non-excited state and to fluidly connect the cuff and the forced release opening with each other in an excited state.

6. The cuff pressure adjusting device according to claim 4,
wherein the gas feeding member has first and second ends, and the first end is closer to the electronic display than the second end, and
the manual gas release valve is disposed at the first end of the gas feeding member.

7. The cuff pressure adjusting device according to claim 4,
wherein the controller is configured to switch between a normal operation state and a sleep state of the cuff pressure adjusting device in response to the detected pressure and an elapsing time,
the controller is configured to select the sleep state where at least display on the electronic display is stopped when the cuff pressure detection sensor does not detect the pressure in the cuff that is equal to or more than a predetermined first threshold value within a predetermined period of the elapsing time in the normal operation state in which the cuff pressure adjusting device normally works; and
after the controller has selected the sleep state, the controller is configured to select the normal operation state when the cuff pressure detection sensor detects the pressure in the cuff that is equal to or more than a predetermined second threshold value.

8. The cuff pressure adjusting device according to claim 7,
wherein the controller is configured to make the cuff pressure adjusting device return to the normal operation state from the sleep state when the pressing manipulation detection switch detects the pressing manipulation.

9. The cuff pressure adjusting device according to claim 4,
wherein the cuff pressure adjusting device is configured to be activated when the pressing manipulation detection switch detects the pressing manipulation.

10. The cuff pressure adjusting device according to claim 4, wherein the cuff pressure detection sensor includes two pressure sensors, the controller is configured to detect an abnormality state of the cuff pressure adjusting device when the controller determines that a difference between outputs from the two pressure sensors exceeds a predetermined range, and the controller is configured to control a backlight of the electronic display and sound an alarm when the controller detects the abnormality state.

11. The cuff pressure adjusting device according to claim 4, wherein the controller is configured to control a backlight of the electronic display so as to change a light emitting mode corresponding to the detected pressure by the cuff pressure detection sensor.

12. The cuff pressure adjusting device according to claim 11, wherein the light emitting mode corresponds to changing of a color for a light emitting from the backlight, and the color is changed in response to the detected pressure.

* * * * *